United States Patent
Watson et al.

(10) Patent No.: US 12,268,695 B2
(45) Date of Patent: *Apr. 8, 2025

(54) BETULIN-CONTAINING BIRCH BARK EXTRACTS AND THEIR FORMULATION

(71) Applicant: Amryt Pharmaceuticals Designated Activity Company, Dublin (IE)

(72) Inventors: John Ashleigh Watson, Walenstadt (CH); Sebastian Jäger, Wiernsheim (DE); Tobias Zahn, Pforzheim (DE)

(73) Assignee: Amryt Pharmaceuticals Designated Activity Company, Dublin (IE)

( * ) Notice: Subject to any disclaimer, the term of this patent is extended or adjusted under 35 U.S.C. 154(b) by 4 days.

This patent is subject to a terminal disclaimer.

(21) Appl. No.: 18/492,536

(22) Filed: Oct. 23, 2023

(65) Prior Publication Data

US 2024/0050445 A1 Feb. 15, 2024

Related U.S. Application Data

(63) Continuation of application No. 17/686,807, filed on Mar. 4, 2022, now Pat. No. 11,826,374, which is a continuation of application No. 17/393,171, filed on Aug. 3, 2021, now Pat. No. 11,266,660, which is a continuation of application No. 17/120,678, filed on Dec. 14, 2020, now Pat. No. 11,083,733, which is a continuation of application No. 16/959,098, filed as application No. PCT/EP2019/050186 on Jan. 4, 2019, now abandoned.

(60) Provisional application No. 62/613,646, filed on Jan. 4, 2018.

(51) Int. Cl.

| | | |
|---|---|---|
| *A61K 31/56* | (2006.01) | |
| *A61K 31/045* | (2006.01) | |
| *A61K 36/185* | (2006.01) | |
| *A61L 15/44* | (2006.01) | |
| *A61L 26/00* | (2006.01) | |
| *A61K 9/00* | (2006.01) | |
| *A61K 9/06* | (2006.01) | |
| *A61K 9/107* | (2006.01) | |
| *A61K 9/12* | (2006.01) | |
| *A61K 45/06* | (2006.01) | |

(52) U.S. Cl.
CPC ............ *A61K 31/56* (2013.01); *A61K 31/045* (2013.01); *A61K 36/185* (2013.01); *A61L 15/44* (2013.01); *A61L 26/0066* (2013.01); *A61K 9/0014* (2013.01); *A61K 9/06* (2013.01); *A61K 9/107* (2013.01); *A61K 9/122* (2013.01); *A61K 45/06* (2013.01); *A61K 2236/00* (2013.01); *A61L 2300/30* (2013.01)

(58) Field of Classification Search
CPC .................................................. A61K 31/56
See application file for complete search history.

(56) References Cited

U.S. PATENT DOCUMENTS

| | | |
|---|---|---|
| 2,764,620 A | 9/1956 | Findlay |
| 3,489,690 A | 1/1970 | Lachampt et al. |
| 4,044,031 A | 8/1977 | Johansson et al. |
| 4,265,824 A | 5/1981 | Koskenniska et al. |
| 4,481,185 A | 11/1984 | Grollier et al. |
| 4,732,708 A | 3/1988 | Ekman et al. |
| 4,933,177 A | 6/1990 | Grollier et al. |
| 5,166,176 A | 11/1992 | Obagi et al. |
| 5,248,807 A | 9/1993 | Fujimoto et al. |
| 5,466,452 A | 11/1995 | Whittle |
| 5,567,419 A | 10/1996 | Togiya et al. |
| 5,647,976 A | 7/1997 | Rothe et al. |
| 5,660,727 A | 8/1997 | Gleave et al. |
| 5,750,578 A | 5/1998 | Carlson et al. |
| 5,753,493 A | 5/1998 | Wiersma |
| 5,780,196 A | 7/1998 | Fujiwara et al. |
| 5,785,856 A | 7/1998 | Gleave et al. |
| 5,843,311 A | 12/1998 | Richter et al. |
| 5,882,916 A | 3/1999 | Wiersma |
| 6,008,246 A | 12/1999 | Ito et al. |
| 6,022,890 A | 2/2000 | Bao et al. |
| 6,124,362 A | 9/2000 | Bradbury et al. |
| 6,175,035 B1 | 1/2001 | Draeger et al. |
| 6,187,323 B1 | 2/2001 | Aiache et al. |
| 6,264,998 B1 | 7/2001 | Ramadoss et al. |
| 6,280,778 B1 | 8/2001 | Gaudet et al. |
| 6,342,208 B1 | 1/2002 | Hyldgaard et al. |

(Continued)

FOREIGN PATENT DOCUMENTS

| | | |
|---|---|---|
| CA | 2385139 A1 | 4/2001 |
| CN | 101664562 A | 3/2010 |

(Continued)

OTHER PUBLICATIONS

Amryt Pharma: "Phase III Efficacy and Safety Study of Oleogei-S10 in Epidermolysis Bullosa", ClinicaiTrials.gov, Sep. 22, 2022 (Sep. 22, 2022), XP055983106, Retrieved from the Internet: URL: https://clinicaltrials.gov/ct2/show/NCT03068780, 5 pages.

Atherton et al, "Epidermolysis Bullosa: An outline for professionals." Great Ormond Street Hospital for Children, London, England, Nov. 2003, 1 page.

Barret, J.P., "Accelerated re-epithelialization of partial-thickness skin wounds by a topical betulin gel: Results of a randomized phase III clinical trials program." Burns (Sep. 2017); 43(6): 1284-1294. Epub Apr. 8, 2017.

Broughton II, et al., "Wound Healing: An Overview." Plastic and Reconstructive Surgery (Jun. 2006); 117: 1e-S-4eS, 4 pages.

(Continued)

*Primary Examiner* — Svetlana M Ivanova
(74) *Attorney, Agent, or Firm* — COOLEY LLP

(57) ABSTRACT

The present disclosure relates to birch bark extracts, methods of producing such extracts, stable pharmaceutical compositions containing such extracts and methods of using of such extracts. The birch bark extracts of the present disclosure contain triterpenes, which are known to improve wound healing.

30 Claims, 2 Drawing Sheets

(56) References Cited

U.S. PATENT DOCUMENTS

Figure 1:
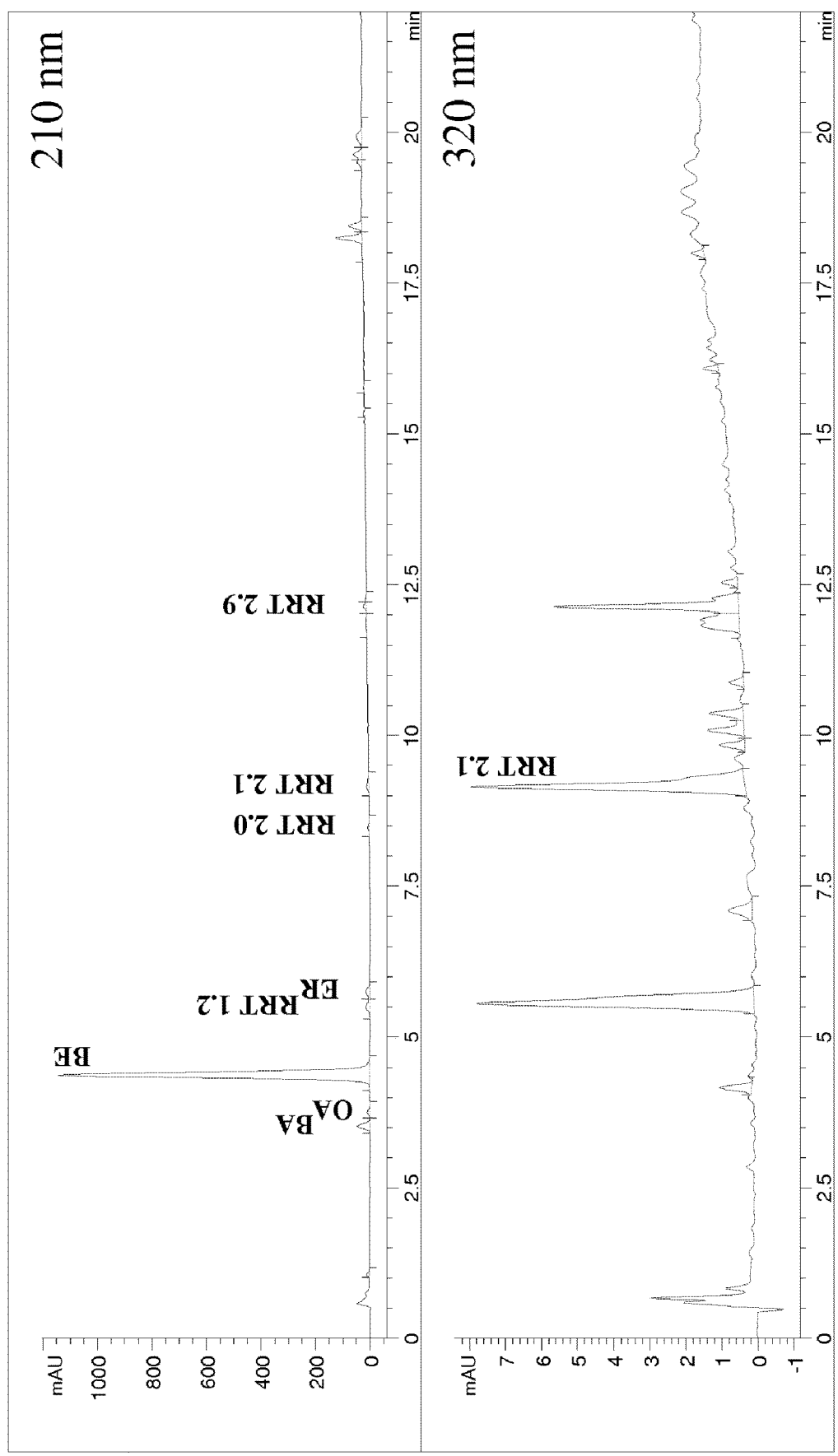

| | | | |
|---|---|---|---|
| 6,392,070 | B1 | 5/2002 | Krasutsky et al. |
| 6,403,816 | B1 | 6/2002 | Jaggi et al. |
| 6,682,763 | B2 | 1/2004 | Kuno et al. |
| 6,746,695 | B1 | 6/2004 | Martin et al. |
| 7,482,383 | B2 | 1/2009 | Scheffler |
| 7,799,352 | B2 | 9/2010 | Nho et al. |
| 8,536,380 | B2 | 9/2013 | Scheffler |
| 8,828,444 | B2 | 9/2014 | Scheffler |
| 9,352,041 | B2 | 5/2016 | Scheffler |
| 9,827,214 | B2 | 11/2017 | Scheffler |
| 11,083,733 | B2* | 8/2021 | Watson ............... A61L 15/44 |
| 11,266,660 | B2* | 3/2022 | Watson ............... A61K 31/045 |
| 11,826,374 | B2* | 11/2023 | Watson ............... A61L 26/0066 |
| 2001/0038878 | A1 | 11/2001 | Bhaggan et al. |
| 2002/0119935 | A1 | 8/2002 | Krasutsky et al. |
| 2002/0128210 | A1 | 9/2002 | Krasutsky et al. |
| 2003/0087789 | A1 | 5/2003 | Scheffler |
| 2003/0108624 | A1 | 6/2003 | Kosbab |
| 2003/0124158 | A1 | 7/2003 | Heidenfelder et al. |
| 2003/0133958 | A1 | 7/2003 | Kuno et al. |
| 2004/0146477 | A1 | 7/2004 | Meffert et al. |
| 2005/0019426 | A1 | 1/2005 | Wirth et al. |
| 2007/0231418 | A1 | 10/2007 | Scheffler |
| 2007/0299285 | A1 | 12/2007 | Scheffler |
| 2009/0131714 | A1 | 5/2009 | Krasutsky et al. |
| 2009/0166178 | A1 | 7/2009 | Harmon et al. |
| 2012/0231054 | A1 | 9/2012 | Scheffler |
| 2012/0315315 | A1 | 12/2012 | Neubourg |
| 2014/0050790 | A1 | 2/2014 | Scheffler |
| 2016/0317481 | A1 | 11/2016 | Scheffler |
| 2018/0263937 | A1 | 9/2018 | Scheffler |
| 2018/0296508 | A1 | 10/2018 | Scheffler |
| 2019/0183797 | A1 | 6/2019 | Daniels et al. |
| 2020/0330481 | A1 | 10/2020 | Watson et al. |
| 2021/0093647 | A1 | 4/2021 | Watson et al. |
| 2021/0369733 | A1 | 12/2021 | Watson et al. |
| 2022/0184097 | A1 | 6/2022 | Watson et al. |

FOREIGN PATENT DOCUMENTS

| | | |
|---|---|---|
| CN | 103439446 A | 12/2013 |
| CN | 107158156 A | 9/2017 |
| DE | 3207005 A1 | 9/1982 |
| DE | 4318280 A1 | 12/1993 |
| DE | 19544905 A1 | 6/1997 |
| DE | 10056902 A1 | 5/2002 |
| DE | 10317400 A1 | 11/2004 |
| DE | 10329955 A1 | 2/2005 |
| DE | 19713768 B4 | 7/2006 |
| EP | 1410790 A1 | 4/2004 |
| EP | 1526906 A1 | 5/2005 |
| EP | 1872788 A1 | 1/2008 |
| ES | 2279136 T3 | 8/2007 |
| ES | 2576832 T3 | 7/2016 |
| JP | S5742326 A | 3/1982 |
| JP | S597106 A | 1/1984 |
| JP | S5967212 A | 4/1984 |
| JP | S59206496 A | 11/1984 |
| JP | S61205204 A | 9/1986 |
| JP | H02169507 A | 6/1990 |
| JP | H054911 A | 1/1993 |
| JP | H0597106 A | 4/1993 |
| JP | H09235293 A | 9/1997 |
| JP | H10152444 A | 6/1998 |
| JP | 2002138014 A | 5/2002 |
| JP | 2003146865 A | 5/2003 |
| JP | 2003335627 A | 11/2003 |
| JP | 2004107227 A | 4/2004 |
| JP | 2004519411 A | 7/2004 |
| JP | 2008037871 A | 2/2008 |
| JP | 2009506981 A | 2/2009 |
| JP | 2017505298 A | 2/2017 |
| RU | 2635533 C1 | 11/2017 |
| WO | WO-9832443 A1 | 7/1998 |
| WO | WO-9834603 A1 | 8/1998 |
| WO | WO-0062751 A2 | 10/2000 |
| WO | WO-0103712 A1 | 1/2001 |
| WO | WO-0110885 A2 | 2/2001 |
| WO | WO-0119365 A1 | 3/2001 |
| WO | WO-0172315 A1 | 10/2001 |
| WO | WO-03043594 A2 | 5/2003 |
| WO | WO-2004016336 A1 | 2/2004 |
| WO | WO-2005123037 A1 | 12/2005 |
| WO | WO-2006133395 A2 | 12/2006 |
| WO | WO-2006135493 A2 | 12/2006 |
| WO | WO-2008046541 A2 | 4/2008 |
| WO | WO-2008055143 A2 | 5/2008 |
| WO | WO-2009090394 A2 | 7/2009 |
| WO | WO-2011064271 A2 | 6/2011 |
| WO | WO-2011107522 A2 | 9/2011 |
| WO | WO-2015104544 A1 | 7/2015 |
| WO | WO-2017147067 A1 | 8/2017 |
| WO | WO-2018017576 A1 | 1/2018 |
| WO | WO-2019134982 A1 | 7/2019 |

OTHER PUBLICATIONS

Castro and Robles, "Procesamiento y caracterización del gel de Aloe vera para la elaboración de hidrogeles, [Processing and characterization of Aloe vera gel for the production of hydrogels]." 2007. Instituto Peruano de Energía Nuclear (IPEN), (Peruvian Institute of Nuclear Energy). pp. 235-241. Available at: https://repositorio.ipen.gob.pe/handle/20.500.13054/521. With English abstract, 8 pages.

Castro, et al., "Descontaminacion por radiacion gamma y caracterizacion de un gel de Aloe vera: Reporte Preliminar [Decontamination by gamma radiation and characterization of a gel of Aloe vera: Preliminary Report]", Instituto Peruano de Energía Nuclear (Peruvian Institute of Nuclear Energy), Nov. 2008, pp. 225-228. With English translation, 7 pages.

Committee for Proprietary Medicinal Products (CPMP): "Decision Trees for the Selection of Sterilisation Methods Annex to Note for Guidance on Development Pharmaceutics (CPMP/QWP/155/96) Discussion in the Quality Working Party", The European Agency for the Evaluation of Medicinal Products Evaluation of Medicines for Human Use, Apr. 5, 2000 (Apr. 5, 2000), XP055983066, 4 pages.

Daniels, et al., "Betulin fur tensidfreie Emulsionen, [Betulin for surfactant-free emulsions]", Pharmazeutische Zeitung, Govi Verlag, Eschborn, DE, vol. 153, No. 13, Mar. 1, 2008 (Mar. 1, 2008), pp. 34-35, ISSN: 0031-7136, with English translation, 11 pages.

Del Carmen Recio, M., et al., "Investigations on the steroidal anti-inflammatory activity of triterpenoids from Diospyros leucomelas," Planta Med. 61: 9-12, (1995), 4 pages.

Eckermann, C., et al., "Comparison of solvents for extraction and crystallization of betulinol from birch bark waste," Paperi ja Puu—Papper och Tra 3: 100-106, (1985).

Ekman, R., "Lipophilic Extractives of the Inner Bark of Birch, Betula verrucosa Ehrh.," Finn. Chem. Letters, p. 162, (1983b). 4 pages.

Ekman, R., "The Suberin Monomers and Triterpenoids from the Outer Bark of Betula verrucosa Ehrh.," Holzforschung, 37: 205-211, (1983a). 7 pages.

European Medicines Agency. Science Medicines Health, Assessment Report, Episalvan, Nov. 19, 2015, EMA/833320/2015, 104 pages.

Evers, M. et al., "Betulinic acid derivates: a new class of human immunodeficiency virus type 1, specific inhibitors with a new mode of action." J. Med. Chem. 39: 1056-1068 (1996).

Extended European Search Report for EP Application No. 17831691.5, dated Dec. 11, 2019, 7 pages.

Extended European Search Report for European Application No. EP23173906.1 dated Oct. 26, 2023, 12 pages.

Färber and Daniels, "Ex vivo Skin Permeation of Betulin from Water-in-Oil Foams." Skin Pharmacol Physiol. (2016); 29(5): 250-256. Epub Sep. 16, 2016.

German Office Action issued in Patent Application No. 11246367, dated Sep. 9, 2010; 4 pages (English translation).

(56) References Cited

OTHER PUBLICATIONS

Grysko, M. et al. (2013) "Evaluation of the mechanism of gelation of an oleogel based on atriterpene extract from the outer bark of birch." Pharmazie, 68: 572-577.

Harish, B.G., et al. (2008) "Wound Healing activity and docking of glycogen-synthasekinase-3—protein with isolated triterpenoid Lupeol in rats." Phytomedicine, 15: 763-767.

Hausmann, U., "Beiträge zur Kenntnifs des Betulins. Auszug aus Verfassers Inaugural Dissertation, Gttingen 1876 [On betulin. Excerpt from the author's Ph.D thesis, Gttingen 1876]." Annalen der Chemis, 182: 368-380 (with English translation, 20 pages).

Hayek, E.W. et al., "A Bicentennial of Betulin." Phytochemistry, 28(9): 2229-2242 (1989).

Hua, Y. et al., "Triterpenes From the Outer Bark of Betula Nigra," Journal of Wood Chemistry and Technology 11 (4): 503-516 (1991).

Huneck, S., et al., "3β-Acetoxyhopan-1β,22-diol, a triterpene from the lichen Pseudoparmelia texana", Phytochemistry, 22(9): 2027-2030, 1983.

Huyke Constance, et al: "Treatment of actinic keratoses with a novel betulin-based oleogel. A prospective, randomized, comparative pilot study." J Dtsch Dermatol Ges. Feb. 2009; 7(2): 128-133.

International Atomic Energy Agency (IAEA), "Manual on Radiation Sterilization of Medical and Biological Materials." International Atomic Energy Agency Vienna, 1973. Available at: https://inis.iaea.org/collection/NCLCollectionStore/_Public/05/105/5105679.pdf., 343 pages.

International Patent Application No. PCT/EP2010/068157, International Search Report and Written Opinion (and English translation), dated Jan. 16, 2012, 22 pages.

International Patent Application No. PCT/US2017/042610, International Preliminary Report on Patentability, dated Jan. 22, 2019, 7 pages.

International Patent Application No. PCT/US2017/042610, International Search Report and Written Opinion, mailed Oct. 2, 2017, 9 pages.

International Search Report and Written Opinion for International Application No. PCT/EP2019/050186, mailed Mar. 29, 2019, 17 pages.

Jaeger, et al., "Pharmakologie ausgewhlter Terpene." In: Pharmazeutische Zeitung, 2006, vol. 151, S. 16-25. (German).

Jäger Sebastian and Zahn Tobias: "The new wound healing drug EPISALVAN: formulation and study design Das neue Wund-Arzneimittel Episalvan®: Galenik und Studiendesign." PHARMAKON, vol. 4, No. 4, Jul. 2016, pp. 349-355, with English translation.

Jääskeläinen, P., "Betulinol and its utilisation," Paperi ja Puu—Papper och Tr 10: 599-603, (1981).

Lasczyk, Melanie (2007) "Triterpentrockenextrakt aus Birkenkork (Betula alba cortex). Untersuchungen zur chemischen Zusammensetzung, Galenik, Penetration und pharmakologisch-biologischen Wirkung." Albert Ludwig University of Freiburg, Doctorate Dissertation; 172 total pages (German).

Laszczyk, M. et al. (2006) "Physical, Chemical and Pharmacological Characterization of a New Oleogel-Forming Triterpene Extract from the Outer Bark of Birch (Betulae Cortex)." Planta Med, 72(15): 1389-1395.

Laszczyk, M. et al. (2009) "Topical therapy with the betulin based triterpene extract (TE) in patients with chronic pruritus" Presented at the 57th International Congress and Annual Meeting of the Society for Medicinal Plant and Natural Product Research; Geneva, Switzerland, Aug. 16-20, 2009. Planta Medica, 75(09): Abstract PI16, DOI: 10.1055/s-0029-1234780. 1 page.

Lowitz, M., "On a novel, almost benzoin-like, substance from birches," Chemische Analysen, Hrsg. Grell, L., 2: 312 (and English translation), 5 pages.

Maquart, Francois-Xavier, et al., "Stimulation of Collagen Synthesis in Fibroblast Cultures by a Triterpene Extracted From Centella Asiatica", Connective Tissue Research: An Internat. Healthcare, US, Bd, 24, Jan. 1, 1990, vol. 24, pp. 107-120.

Nowak, G. A., "Cosmetic and Medicinal Properties of the Birch", Amer. Perfumer Cosmet., 81: 37, (1966). 2 pages.

O'Connell, M.M. et al., "Betulin and Lupeol in Bark from four white-barked birches," Phytochemistry 7: 2175-2176, (1988).

Pârvanescu et al., "Oleogel Formulations for the Topical Delivery of Betulin and Lupeol in Skin Injuries—Preparation, Physicochemical Characterization, and Pharmaco-Toxicological Evaluation," Molecules, vol. 26, 4174, Jul. 9, 2021, 22 pages.

Palla, Camila, et al., "Multi-objective optimization of high oleic sunflower oil and monoglycerides oleogels: Searching for rheological and textural properties similar to margarine." Food structure 12 (2017): 1-14.

Schwieger-Briel, A, et al., "Betulin-Based Oleogel to Improve Wound Healing in Dystrophic Epidermolysis Bullosa: A Prospective Controlled Proof-of-Concept Study", Dermatology Research and Practice, 2017, vol. 2017, Article ID 5068969, 10 pages.

Shrikhande, B.K., et al. (Dec. 1, 2001) "Development and Evaluation of Antiinflammatory Oleogels of Bosewellia Serrate (GUGUL) and Curcuma longa (Turmeric)." Indian Drugs, Indian Drug Manufacturers Association; 38(12): 613-616.

Shukla, et al., "In vitro and in vivo wound healing activity of asiaticoside isolated from Gentelia asiatica", Journal of Ethnopharmacology (1999); 65: 1-11.

Steinbrenner Isabel et al., "Influence of the Oil Phase and Topical Formulation on the Wound Healing Ability of a Birch Bark Dry Extract", May 24, 2016, PLOS One, vol. 11, No., 5, e0155582, doi: 10.1371/journal.pone.0155582 , pp. 1-17.

Sun, I-Chen, et al., "Anti-AIDS Agents, 32, Synthesis and anti-HIV activity of Betulin derivates," Bioorganic & Medical Chemistry Letters 8: 1267-1272, (1998).

Tolstikov, et al., "Betulin and its derivatives, Chemistry and biological activity." Chemistry for Sustainable Development (2005); 13: 1-29.

Ukkonen, K., et al., "Birch Bark Extractives," Kemia-Kemi (1979); 5: 217-220.

Wheeler, "The Preparation of Betulin by Sublimation", Pharmaceutical Journal (Nov. 1899); 494: 353, 1 page.

Yasukawa, K., et al., "Sterol and triterpene derivates from plants Inhibit the Effects of Tumor Promoter, and Sisterol and Betulinic Acid Inhibit Tumor Formation in Mouse Skin Two-Stage Carcinogenesis," Oncogene 48: 72-76 (1991).

Zahn, T., et al., "Birkenrindenextrakt zur Wundheilung", Deutsche Apotheker Zeitung, Nov. 23, 2017 (Nov. 23, 2017), Retrieved from the Internet: URL: https://www.deutsche-apotheker-zeitung.de/daz-az/2017/daz-47-2017/birkenrindenextrakt-zur-wundheilung, with machine translation, 10 pages.

Zhang et al., "Radiation Sterilization", Traditional Chinese Pharmacy for the major of Chinese Materia Medica, New Century 2nd edition. China Press of Traditional Chinese Medicine, Mar. 2017. pp. 44, and English translation, 6 pages.

Zhao Guoling, et al: "Simultaneous determination of betulin and betulinic acid in white birch bark using RP-HPLC", Journal of Pharmaceutical and Biomedical Analysis, 2007, vol. 43, pp. 959-962.

\* cited by examiner

BETULIN-CONTAINING BIRCH BARK EXTRACTS AND THEIR FORMULATION

CROSS-REFERENCE TO RELATED APPLICATIONS

This application is a continuation of U.S. application Ser. No. 17/686,807, filed Mar. 4, 2022, which is a continuation of U.S. application Ser. No. 17/393,171, filed Aug. 3, 2021, now U.S. Pat. No. 11,266,660, which is a continuation of U.S. application Ser. No. 17/120,678, filed Dec. 14, 2020, now U.S. Pat. No. 11,083,733, which is a continuation of U.S. application Ser. No. 16/959,098, filed Jun. 29, 2020, which is a U.S. National Stage Application under 35 U.S.C. § 371 of International Application No. PCT/EP2019/050186, filed Jan. 4, 2019, which claims the benefit of priority to U.S. Provisional Application No. 62/613,646, filed Jan. 4, 2018, the entire contents of which are hereby incorporated by reference in their entireties for all purposes.

FIELD OF THE DISCLOSURE

The present disclosure relates to pharmaceutical formulations derived from the extracts of birch bark.

BACKGROUND OF THE DISCLOSURE

The triterpenes found in birch bark extracts are known to have wound healing properties. Methods of extracting these triterpenes from birch bark are reported in U.S. Pat. No. 7,482,383. These methods provide solid birch bark extracts that may be used in pharmaceutical formulations. For example, emulsions containing such extracts are described in U.S. Pat. No. 7,482,383, and oleogels containing such extracts are described in U.S. Pat. Nos. 9,352,041; 8,828,444 and 8,536,380.

For clinical use in wound healing, an oleogel must be applied by touch to the area of the skin where treatment is needed. Touch application is disadvantageous for the treatment of certain skins conditions (e.g., epidermolysis bullosa) because the simple act of applying the oleogel may lead to worsening of the skin condition.

Therefore, there is a need for wound-healing formulations containing solid birch bark extracts that may be applied to the skin without worsening the patient's condition.

The present disclosure provides clinically-advantageous wound-healing formulations (including oleogels, emulsions and foams) with improved rheological properties which overcome the disadvantages of the known solid birch bark-containing emulsions and oleogels.

SUMMARY OF THE DISCLOSURE

The present disclosure provides a solid birch bark extract that contains at least about 70% by weight of betulin and one or more triterpenes selected from the group consisting of betulinic acid, oleanolic acid, erythrodiol and lupeol. The solid birch bark extracts described herein may be formulated in an oleogel that possesses clinically-advantageous rheological properties.

The present disclosure also provides a method of making a solid birch bark extract that may be dispersed in a nonpolar solvent to provide a clinically-advantageous oleogel comprising the steps of (a) contacting birch bark with a suitable solvent to form an extraction solution containing betulin and at least one triterpene; (b) separating the birch bark from the extraction solution; (c) cooling the extraction solution to crystallize a portion of the betulin and triterpene from the solution; (d) separating the crystallized betulin and triterpene; (e) drying the separated, crystallized betulin and triterpene to form a solid birch bark extract. The present disclosure also provides the solid birch bark extracts that are prepared according to these methods.

The present disclosure provides a clinically-advantageous oleogel comprising about 1% to about 20% by weight of particles of the solid birch bark extract dispersed in about 80% to about 99% of one or more nonpolar liquids the solid birch bark extracts are dispersed in a suitable nonpolar liquid to form an oleogel. A sterile wound dressing comprising a pad and a therapeutically effective amount of the oleogel is also provided.

The present disclosure provides an emulsion comprising an oleogel of the present invention and further provides a foam comprising an emulsion of the present disclosure.

The present disclosure also provides methods of treating a wound in a patient by topically administering an effective amount of an oleogel, an emulsion or a foam of the present disclosure to at least a portion of the wound.

The present disclosure also provides methods of treating epidermolysis bullosa in a patient in need thereof comprising topically administering an effective amount of an oleogel, an emulsion or a foam of the present disclosure to an area of epidermolysis bullosa of the patient.

The present disclosure provides a solid birch bark extract, oleogel, sterile wound dressing, process of preparation, emulsion, foam, pressurized container, method of treating a wound, and method of treating epidermolysis bullosa according to the following numbered embodiments:

1. A solid birch bark extract comprising at least about 70 wt. % betulin and one or more triterpenes selected from the group consisting of betulinic acid, oleanolic acid, erythrodiol, and lupeol.
2. The sold birch bark extract of embodiment 1, wherein the solid birch extract has an HPLC chromatogram substantially identical to FIG. 1 when chromatographed according to the following HPLC method:

| Time (min) | Acetonitrile | Water | $H_3PO_4$ (v/v) | Flow rate (ml/min) |
|---|---|---|---|---|
| 0 | 30 | 70 | 0.1% | 0.6 |
| 5 | 30 | 30 | 0.1% | 0.6 |
| 15 | 98 | 2 | 0.1% | 0.6 |
| 20 | 98 | 2 | 0.1% | 0.6 |
| 21 | 30 | 70 | 0.1% | 0.6 |
| 30 | 30 | 70 | 0.1% | 0.6 |

Column C18, 2.6 μm, 150×2.1 mm; detector: 210 and 320 nm;

wherein the betulinic acid has a relative retention time of about 0.75-0.90, the oleanolic acid has a relative retention time of about 0.84-0.97, the betulin has a relative retention time of 1.00, the erythrodiol has a relative retention time of about 1.25-1.40, and the lupeol has a relative retention time of about 3.50-4.15.

3. The solid birch bark extract of embodiment 1 or 2, prepared by a process comprising:
   (a) contacting birch bark with a pharmaceutically acceptable solvent, thereby forming an extraction solution comprising betulin and one or more triterpenes;
   (b) separating the birch bark from the extraction solution;

(c) cooling the extraction solution whereby a portion of the betulin and one or more triterpenes crystallizes from the cooled extraction solution;

(d) separating the crystallized betulin and one or more triterpenes from the cooled extraction solution;

(e) drying the separated, crystallized betulin and one or more triterpenes to provide the solid birch bark extract;

wherein if after drying, about 1 wt. % to about 20 wt. % of the dried solid birch bark extract of step (e) dispersed in refined sunflower oil forms an oleogel.

4. The solid birch bark extract of embodiment 3, wherein one or more of steps (a), (c), and (e) is carried out under the following conditions:
   (i) said contacting of step (a) is carried out at a temperature of about 60° C. to about 130° C.;
   (ii) said cooling of step (c) is carried out at a temperature of about −20° C. to about 35° C.;
   (iii) said drying of step (e) is carried out at a temperature of about 75° C. to about 95° C. at a pressure of less than about 70 mbar.

5. The solid birch bark extract of embodiment 3, wherein two or more of steps (a), (c), and (e) are carried out under the following conditions:
   (i) said contacting of step (a) is carried out at a temperature of about 60° C. to about 130° C.;
   (ii) said cooling of step (c) is carried out at a temperature of about −20° C. to about 35° C.;
   (iii) said drying of step (e) is carried out at a temperature of about 75° C. to about 95° C. at a pressure of less than about 70 mbar.

6. The solid birch bark extract of embodiment 3, wherein steps (a), (c), and (e) are carried out under the following conditions:
   (i) said contacting of step (a) is carried out at a temperature of about 60° C. to about 130° C.;
   (ii) said cooling of step (c) is carried out at a temperature of about −20° C. to about 35° C.;
   (iii) said drying of step (e) is carried out at a temperature of about 75° C. to about 95° C. at a pressure of less than about 70 mbar.

7. The solid birch bark extract of any one of embodiments 3-6, wherein the pharmaceutically acceptable solvent is a hydrocarbon or alcohol, or combinations thereof.

8. The solid birch bark extract of any one of embodiments 3-7, wherein the pharmaceutically acceptable solvent is a hydrocarbon selected from the group consisting of n-pentane, n-hexane, or n-heptane.

9. The solid birch bark extract of embodiment 8, wherein the pharmaceutically acceptable solvent is n-heptane, and said contacting is carried out at a temperature of about 60° C. to about 130° C. for about 8-12 minutes.

10. The solid birch bark extract of any one of embodiments 3-9, wherein in step (c) the cooled extraction solution is supersaturated at least about 2-fold.

11. The solid birch bark extract of embodiment 10, wherein the cooled extraction solution is supersaturated about 5-fold.

12. The solid birch bark extract of any of embodiments 3-11, wherein the amount of residual extraction solvent is no more than about 0.5 wt. %.

13. An oleogel comprising about 1 wt. % to about 20 wt. % of particles of the solid birch bark extract of any one of embodiments 1-12, having an average particle size of less than about 50 μm, dispersed in about 80 wt. % to about 99 wt. % of one or more nonpolar liquids.

14. The oleogel of embodiment 13, wherein the dispersed solid birch bark extract particles are the only oleogel forming agent in the oleogel.

15. The oleogel of embodiment 13 or 14, comprising about 10 wt. % of particles of the solid birch bark extract.

16. The oleogel of any one of embodiments 13 to 15, wherein the nonpolar liquid comprises at least one triglyceride.

17. The oleogel of any one of embodiments 13 to 16, wherein the nonpolar liquid comprises at least one C7 or greater hydrocarbon.

18. The oleogel of embodiment 16, wherein the nonpolar liquid comprises one or more vegetable oils.

19. The oleogel of embodiment 18, wherein the nonpolar liquid comprises sunflower oil.

20. The oleogel of any one of embodiments 13-19, wherein the nonpolar liquid has a peroxide value less than about 10.

21. The oleogel of embodiment 20, wherein the peroxide value is no more than about 3.

22. The oleogel of any one of embodiments 13-21, wherein the oleogel is substantially free of solid birch bark extract particles having a size greater than about 50 μm.

23. The oleogel of any one of embodiments 13-22, wherein the oleogel is sterile.

24. The oleogel of embodiment 23, wherein the oleogel is sterilized by ionizing irradiation at doses less than about 20 kGy.

25. The oleogel of embodiment 24, wherein the oleogel is sterilized by ionizing irradiation at doses ranging from about 11 to about 20 kGy.

26. The oleogel of any one of embodiments 13-25, wherein the segregation of the nonpolar liquid from the oleogel is less than about 10% after centrifuging at 25° C. for 30 min at 2750 g.

27. The oleogel of any one of embodiments 13-26, wherein the viscosity at 200/s of the oleogel ranges from about 0.5 to about 4.0 Pa·s and the thixotropy value of the oleogel ranges from about 200 to about 1200 Pa·s as measured according to the rotating viscometer method described in Ph. Eur. 2.2.10 using a cone-plate viscometer.

28. The oleogel of any one of embodiments 13-27, wherein the consistency of the oleogel ranges from about 300-3000 mN as measured according using a texture analyser.

29. The oleogel of any one of embodiments 13-28, further comprising a disinfectant.

30. The oleogel of embodiment 29, wherein the disinfectant is selected from the group consisting of ethanol, n-propanol, and isopropanol.

31. The oleogel of any one of embodiments 13-28, further comprising a lipophilic antibiotic.

32. A sterile wound dressing comprising:
   (a) a pad, and
   (b) a therapeutically effective layer comprising the oleogel of any of embodiments 13-31 disposed on at least one surface of the pad.

33. The sterile wound dressing of embodiment 32, wherein the pad is an absorbent pad.

34. A process for preparing the solid birch bark extract of embodiment 1 or 2, comprising:

(a) contacting birch bark with a pharmaceutically acceptable solvent, thereby forming an extraction solution comprising betulin and one or more triterpenes;

(b) separating the birch bark from the extraction solution;

(c) cooling the extraction solution whereby a portion of the betulin and one or more triterpenes crystallizes from the cooled extraction solution;

(d) separating the crystallized betulin and one or more triterpenes from the cooled extraction solution;

(e) drying the separated, crystallized betulin and one or more triterpenes to provide the solid birch bark extract;

wherein after drying, about 1 wt. % to about 20 wt. % of the dried solid birch bark extract of step (e) dispersed in refined sunflower oil forms an oleogel.

35. The process of embodiment 34, wherein one or more of steps (a), (c), and (e) is carried out under the following conditions:
(i) said contacting of step (a) is carried out at a temperature of about 60° C. to about 130° C.;
(ii) said cooling of step (c) is carried out at a temperature of about −20° C. to about 35° C.;
(iii) said drying of step (e) is carried out at a temperature of about 75° C. to about 95° C. at a pressure of less than about 70 mbar.

36. The process of embodiment 34, wherein two or more of steps (a), (c), and (e) are carried out under the following conditions:
(i) said contacting of step (a) is carried out at a temperature of about 60° C. to about 130° C.;
(ii) said cooling of step (c) is carried out at a temperature of about −20° C. to about 35° C.;
(iii) said drying of step (e) is carried out at a temperature of about 75° C. to about 95° C. at a pressure of less than about 70 mbar.

37. The process of embodiment 34, wherein steps (a), (c), and (e) are carried out under the following conditions:
(i) said contacting of step (a) is carried out at a temperature of about 60° C. to about 130° C.;
(ii) said cooling of step (c) is carried out at a temperature of about −20° C. to about 35° C.;
(iii) said drying of step (e) is carried out at a temperature of about 75° C. to about 95° C. at a pressure of less than about 70 mbar.

38. The process of any one of embodiments 34-37, wherein the pharmaceutically acceptable solvent is a hydrocarbon selected from the group consisting of n-pentane, n-hexane, or n-heptane.

39. The process of any one of embodiments 34-38, wherein the pharmaceutically acceptable solvent is n-heptane, and said contacting is carried out at a temperature of about 115° C. to about 130° C. for about 8-12 minutes.

40. The process of any one of embodiments 34-39, wherein in step (c) the cooled extraction solution is supersaturated at least about 2-fold.

41. The process of embodiment 40, wherein the cooled extraction solution is supersaturated about 5-fold.

42. The process of any of embodiments 34-41, wherein the amount of residual extraction solvent is no more than about 0.5 wt. %.

43. An emulsion comprising the solid birch bark extract of any of embodiments 1-12.

44. An emulsion comprising the oleogel of any of embodiments 13-31.

45. The emulsion of embodiment 43 or 44, wherein said emulsion is a water-in-oil emulsion.

46. The emulsion of embodiment 45, substantially free of emulsifier.

47. The emulsion of any one of embodiments 43-46, consisting essentially of the solid birch bark extract or oleogel, oil, and water.

48. The emulsion of any one of embodiments 44-46, consisting of the oleogel, oil and water.

49. The emulsion of any one of embodiments 43-46, further comprising a disinfectant.

50. The emulsion of embodiment 49, wherein the disinfectant is selected from the group consisting of ethanol, n-propanol, and isopropanol.

51. The emulsion of any one of embodiments 43-46, further comprising a lipophilic antibiotic.

52. A foam comprising the emulsion of any one of embodiments 43-51.

53. The foam of embodiment 52, further comprising a disinfectant.

54. The foam of embodiment 53, wherein the disinfectant is selected from the group consisting of ethanol, n-propanol, and isopropanol.

55. The foam of embodiment 52, further comprising a lipophilic antibiotic.

56. The foam of any of embodiments 52-55, wherein the interfacial surface tension of the emulsion is greater than about 4 mN/m.

57. The foam of any of embodiments 52-56, wherein the foam index is greater than about 2.

58. The foam of embodiment 52, wherein the oleogel consists of about 5 wt. % to about 10 wt. % solid birch bark extract and the emulsion is a water-in-oil emulsion consisting of the oleogel and about 20 wt. % to about 30 wt. % of water.

59. The foam of embodiment 58, wherein the oleogel consists of about 7 wt. % solid birch bark extract and the amount of water in the emulsion is about 25 wt. %.

60. The foam of any of embodiments 52-56, further comprising an emulsifier selected from the group consisting of phosphatidyl choline, polyglyceryl-3-methyl glucose distearate, and combinations thereof.

61. A pressurized container filled with a mixture comprising the emulsion of any one of embodiments 43-51 and a pharmaceutically acceptable propellant, whereby the emulsion forms a foam upon decanting at least a portion of the mixture from the container.

62. A method of treating a wound in a patient comprising topically administering the oleogel of any one of embodiments 13-31 to at least a portion of the wound.

63. The oleogel of any one of embodiments 13-31, for use in a method of treating a wound.

64. The method or oleogel for use of embodiment 63, wherein the wound is selected from the group consisting of a burns, surgical skin lesions, superficial injuries, chronic wounds, pressure ulcers, diabetic foot ulcers, chronic venous ulcers, artery insufficiency ulcers, wounds from aesthetic skin treatments, wounds from ablative laser skin treatments, wounds from chemical peels, wounds from dermabrasion, wounds resulting from adverse drug reactions, wounds resulting from toxic epidermal necrolysis, wounds resulting from Lyell syndrome, wounds resulting from Stevens-Johnson syndrome, and wounds resulting from radiation dermatitis.

65. A method of treating a wound in a patient comprising topically administering the emulsion of any one of embodiments 43-51 to at least a portion of the wound.
66. The emulsion of any one of embodiments 43-51, for use in a method of treating a wound.
67. The method or emulsion for use of embodiment 66, wherein the wound is selected from the group consisting of burns, surgical skin lesions, superficial injuries, chronic wounds, pressure ulcers, diabetic foot ulcers, chronic venous ulcers, artery insufficiency ulcers, wounds from aesthetic skin treatments, wounds from ablative laser skin treatments, wounds from chemical peels, wounds from dermabrasion, wounds resulting from adverse drug reactions, wounds resulting from toxic epidermal necrolysis, wounds resulting from Lyell syndrome, wounds resulting from Stevens-Johnson syndrome, and wounds resulting from radiation dermatitis.
68. A method of treating a wound in a patient comprising topically administering the foam of any one of embodiments 52-60 to at least a portion of the wound.
69. The foam of any one of embodiments 52-60, for use in a method of treating a wound.
70. The method or foam for use of embodiment 69, wherein the wound is selected from the group consisting of burns, surgical skin lesions, superficial injuries, chronic wounds, pressure ulcers, diabetic foot ulcers, chronic venous ulcers, artery insufficiency ulcers, wounds from aesthetic skin treatments, wounds from ablative laser skin treatments, wounds from chemical peels, wounds from dermabrasion, wounds resulting from adverse drug reactions, wounds resulting from toxic epidermal necrolysis, wounds resulting from Lyell syndrome, wounds resulting from Stevens-Johnson syndrome, and wounds resulting from radiation dermatitis.
71. A method of treating epidermolysis bullosa in a patient in need thereof comprising topically administering to an area of epidermolysis bullosa of the patient the oleogel of any one of embodiments 13-31.
72. The oleogel of any one of embodiments 13-31, for use in a method of treating epidermolysis bullosa.
73. A method of treating epidermolysis bullosa in a patient in need thereof comprising topically administering to an area of epidermolysis bullosa of the patient the emulsion of any one of embodiments 43-51.
74. The emulsion of any one of embodiments 43-51, for use in a method of treating epidermolysis bullosa.
75. A method of treating epidermolysis bullosa in a patient in need thereof comprising topically administering to an area of epidermolysis bullosa of the patient the foam of any one of embodiments 52-60.
76. The foam of any one of embodiments 52-60, for use in a method of treating epidermolysis bullosa.

DETAILED DESCRIPTION OF THE DRAWINGS

FIG. 1. shows the HPLC chromatograph taken from a solid birch bark extract monitoring 210 nm (top figure) and 320 nm (bottom figure). The x-axis in FIG. 1 is the retention time (min), and the y-axis is the peak intensity (mAU).

Figure 2:
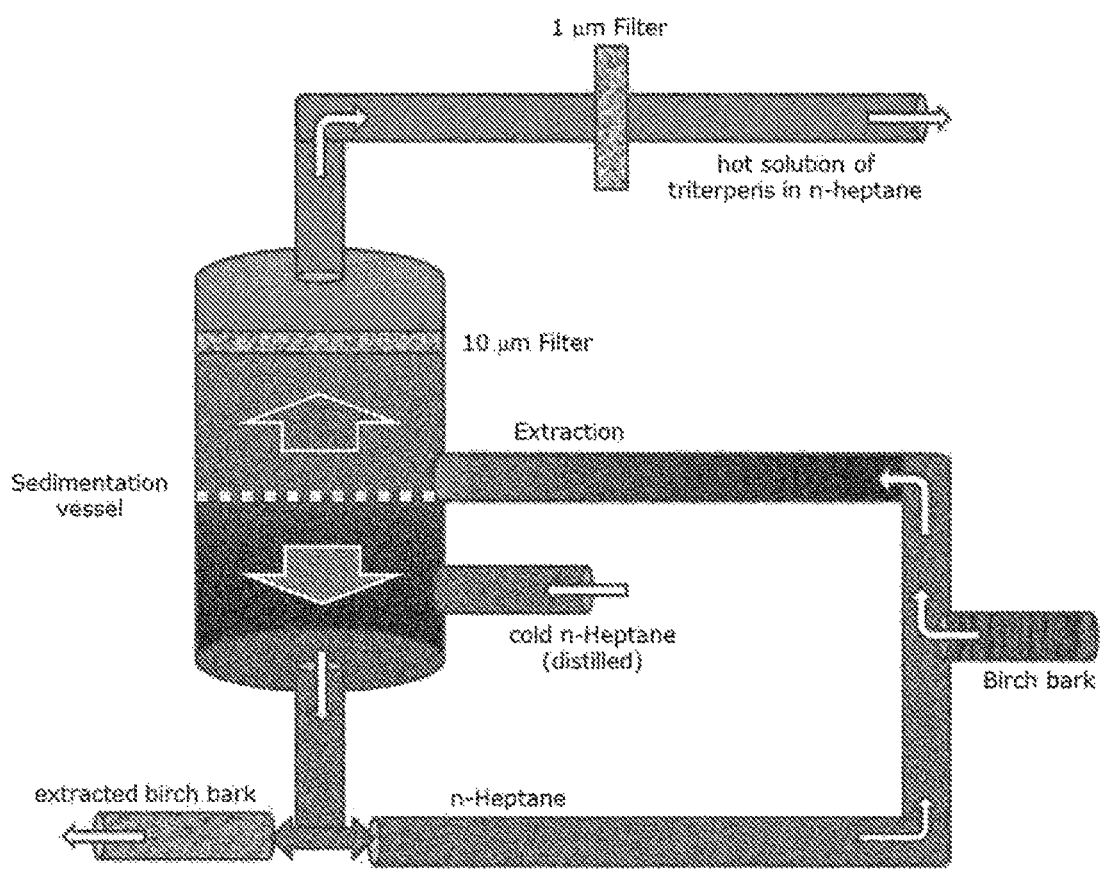

FIG. 2. illustrates the continuous extraction of birch bark to provide an extraction solution comprising betulin and one or more triterpenes.

DETAILED DESCRIPTION OF THE DISCLOSURE

Definitions

While the following terms are believed to be well understood by one of ordinary skill in the art, the following definitions are set forth to facilitate explanation of the presently disclosed subject matter.

It is to be understood that the terminology used herein is for the purpose of describing particular embodiments only and is not intended to be limiting.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure. All references cited herein (including U.S. Pat. Nos. 9,352,041; 8,828,444; 8,536,380; and 7,482,383) are incorporated for all purposes by reference in their entirety.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application. Generally the term "about", as used herein when referring to a measurable value such as an amount of weight, time, dose, etc. is meant to encompass in one example variations of ±15% or ±10%, in another example ±5%, in another example ±1%, and in yet another example ±0.1% from the specified amount, as such variations are appropriate to perform the disclosed method.

"Administering" includes any mode of administration, such as oral, subcutaneous, sublingual, transmucosal, parenteral, intravenous, intra-arterial, buccal, sublingual, topical, vaginal, rectal, ophthalmic, otic, nasal, inhaled, and transdermal. "Administering" can also include prescribing or filling a prescription for a dosage form comprising a particular compound. "Administering" can also include providing directions to carry out a method involving a particular compound or a dosage form comprising the compound.

As used herein, the verb "comprise" as is used in this description and in the claims and its conjugations are used in its non-limiting sense to mean that items following the word are included, but items not specifically mentioned are not excluded.

The term "birch bark" means the cortex of white-barked birch trees. Preferred embodiments include birch bark derived from *Betula pendula* Roth and *Betula pubescens* Ehrh as well as hybrids of both species.

The term "relative retention time" (or "RRT") means ratio of the retention time of the unknown peak to the retention time the betulin peak and is calculated according to the following equation:

$$RRT = RT_{unknown}/RT_{betulin}$$

where $RT_{unknown}$ is the retention time of the unknown peak and $RT_{betulin}$ is the retention time of betulin peak (210 nm) measured by the following HPLC method:

| Time (min) | Acetonitrile | Water | $H_3PO_4$ (v/v) | Flow rate (ml/min) |
|---|---|---|---|---|
| 0 | 30 | 70 | 0.1% | 0.6 |
| 5 | 30 | 30 | 0.1% | 0.6 |
| 15 | 98 | 2 | 0.1% | 0.6 |
| 20 | 98 | 2 | 0.1% | 0.6 |
| 21 | 30 | 70 | 0.1% | 0.6 |
| 30 | 30 | 70 | 0.1% | 0.6 |

Column Phenomenex Kinetix C18, 2.6 µm, 150×2.1 mm.

The term "substantially identical" as used herein means an analytical spectrum, such as HPLC chromatogram, NMR spectrum, and etc., which resembles the reference spectrum to a great degree in both the peak locations and their intensity. For example, a HPLC chromatogram is "substantially identical" to a reference chromatogram if the peak locations (relative retention times) in the HPLC chromatogram vary by no more than ±5% from the peak locations (relative retention times) in the reference chromatogram. In some embodiments, the relative peak intensities in the HPLC chromatogram may vary by no more than ±10% from the peak intensities in the reference chromatogram.

"Therapeutically effective amount" means the amount of an active substance that, when administered to a subject for treating a disease, disorder, or other undesirable medical condition, is sufficient to have a beneficial effect with respect to that disease, disorder, or condition. The therapeutically effective amount will vary depending on the chemical identity and formulation form of the active substance, the disease or condition and its severity, and the age, weight, and other relevant characteristics of the patient to be treated. Determining the therapeutically effective amount of a given active substance is within the ordinary skill of the art and typically requires no more than routine experimentation.

The term "substantially free" means that the ingredient indicated is not present, or is present in only insignificant amounts. In one embodiment, "substantially free" means less than about 10% (e.g. less than about 10 wt. %). In other embodiments, "substantially free" means less than about 5% (e.g. less than about 5 wt. %), less than about 2% (e.g. less than about 2 wt. %), or less than about 1% (e.g. less than about 1 wt. %), or about 0% (e.g. about 0 wt. %). For example, an emulsion that is substantially free of an emulsifier does not contain any emulsifier in a substantial amount (e.g. contains less than about 10 wt. %, less than about 5 wt. %, less than about 2 wt. %, or less than about 1 wt. % of an emulsifier; or contains 0 wt. % of an emulsifier). Similarly, an oleogel that is substantially free of solid birch bark extract particles having a size greater than about 50 µm does not contain any solid birch bark extract particles having a size greater than about 50 µm in a substantial amount (e.g. contains less than about 10 wt. %, less than about 5 wt. %, less than about 2 wt. %, or less than about 1 wt. % of solid birch bark extract particles having a size greater than about 50 µm; or contains 0 wt. % of solid birch bark extract particles having a size greater than about 50 µm).

Solid Birch Bark Extracts

The present disclosure provides solid birch bark extracts that may be formulated in clinically-advantageous oleogels. Without being bound by any theory, it is believed that the chemical composition and the particle morphology of the solid birch bark extracts produced according to the methods of the present disclosure are responsible these advantages.

The solid birch bark extracts of the present disclosure may be characterized on the basis of their chemical composition. In some embodiments, the solid birch bark extracts of the present disclosure comprise lupane and oleanane triterpenes. In particular, the birch bark extracts may contain the lupane triterpenes: betulin, lupeol, and betulinic acid, and the oleanane triterpenes: erythrodiol and oleanolic acid.

The presence of a particular triterpene in the birch extract may be determined using relative retention times obtained from HPLC chromatography. The following HPLC method is used to determine the chemical composition of the solid birch bark extracts of the present disclosure:

| Time (min) | Acetonitrile | Water | $H_3PO_4$ (v/v) | Flow rate (ml/min) |
|---|---|---|---|---|
| 0 | 30 | 70 | 0.1% | 0.6 |
| 5 | 30 | 30 | 0.1% | 0.6 |
| 15 | 98 | 2 | 0.1% | 0.6 |
| 20 | 98 | 2 | 0.1% | 0.6 |
| 21 | 30 | 70 | 0.1% | 0.6 |
| 30 | 30 | 70 | 0.1% | 0.6 |

Column: Phenomenex Kinetix C18, 2.6 µm, 150×2.1 mm.

A Phenomenex Kinetix C18 column is exemplary of an HPLC column having a C-18 modified silica stationary phase on core-shell silica solid support (2.6 µm HILIC 100 Å) with the above noted column dimensions.

When a solid birch bark extract is subjected to the above-mentioned HPLC chromatography method betulinic acid has a relative retention time of about 0.75-0.90, oleanolic acid has a relative retention time of about 0.84-0.97, betulin has a relative retention time of 1.00, erythrodiol has a relative retention time of about 1.25-1.40, and lupeol has a relative retention time of about 3.50-4.15.

In certain embodiments, the solid birch bark extract has an HPLC chromatogram substantially identical to FIG. 1.

In some embodiments, the solid birch bark extract comprises at least about 50 wt. %, at least about 55 wt. %, at least about 60 wt. %, at least about 65 wt. %, at least about 70 wt. %, at least about 75 wt. %, at least about 80 wt. %, at least about 85 wt. %, or at least about 90% by weight betulin and one or more triterpenes. In some embodiments, the one or more triterpenes is selected from the group consisting of betulinic acid, oleanolic acid, erythrodiol and lupeol.

In some embodiments, the solid birch bark extract comprises at least one of the following substances: 3-β-caffeoyl betulin, acetate of the methylester of betulinic acid, acetyloleanolic acid, allobetulin, betulinic aldehyde, betulonic acid, betulonic aldehyde, lupane-3β,20,28-triol, lupane-3β,20-diol (monogynol), oleanolic aldehyde, sitosterol, ursolic acid, or β-amyrin The solid birch bark extract of the present disclosure may be characterized by the particle size of the particles of the solid birch bark extract. In some embodiments, the average particle size of the particles of the solid birch bark extract is less than about 100 µm, less than about 90 µm, less than about 80 µm, less than about 70 µm, less than about 60 µm, less than about 50 µm, less than about 40 µm, less than about 30 µm or less than about 25 µm.

In other embodiments, the solid birch bark extract of the present disclosure is substantially free of solid birch bark extract particles having a particle size greater than about 30 µm, greater than about 40 µm, greater than about 50 µm, greater than about 60 µm, greater than about 70 µm, greater than about 80 µm, greater than about 90 µm or greater than about 100 µm.

In preferred embodiments, the solid birch bark extracts are derived from *Betula pendula* Roth and *Betula pubescens* Ehrh as well as hybrids of both species.

Solid Birch Bark Extract Manufacturing Processes

The present disclosure provides methods for preparing solid birch bark extracts that may be formulated in clinically-advantageous oleogels. In general, the methods include the steps of obtaining birch trees, stripping and processing the bark from said birch trees, contacting the processed birch bark with a suitable solvent to provide an extraction solution comprising betulin and one or more triterpenes, and isolating and drying the birch bark extract comprising betulin and one or more triterpenes from the extraction solution. In some embodiments, the isolated birch bark extract is in the form of a solid.

In some embodiments, the method comprises: (a) contacting birch bark with a pharmaceutically acceptable solvent to form a extraction solution comprising betulin and one or more triterpenes; (b) separating the birch bark from the extraction solution; (c) cooling the extraction solution whereby a portion of the betulin and one or more triterpenes crystallizes from the cooled extraction solution; (d) separating the crystallized betulin and one or more triterpenes from the cooled extraction solution; and (e) drying the separated, crystallized betulin and one or more triterpenes to provide the solid birch bark extract.

In some embodiments, the birch bark used in step (a) is first processed to improve the extraction efficiency of betulin and one or more triterpenes from the birch bark. For example, experiments have shown that the yield of the dry extract from birch bark is highest when the extracted birch bark particles are small. In certain embodiments, the particle size of the birch bark is reduced prior to step (a) using a mill, or other suitable equipment, until the resulting birch bark passes through a sieve with a mesh size of about 1.25 mm.

In some embodiments, the birch bark is contacted with a pharmaceutically acceptable solvent at a temperature of between about 50° C. and about 200° C. In other embodiments, the temperature is between about 60° C. and about 100° C., between about 60° C. and about 110° C., between about 60° C. to about 120° C., between about 60° C. to about 130° C., between about 70° C. to about 130° C., between about 80° C. to about 130° C., between about 90° C. to about 130° C., or between about 100° C. and 150° C. In certain further embodiments, the temperature is between about 115° C. and 130° C.

In some embodiments, the birch bark is contacted with a pharmaceutically acceptable solvent at a pressure between about 2 to 10 bars. In one embodiment, the pressure is about 4.5 bars.

Pharmaceutically acceptable solvents are known to those of skill in the art and include hydrocarbons, alcohols, ketones, ethers esters, sulfoxides, etc. Examples of pharmaceutically acceptable solvents include, without limitation, 1-butanol, 1-pentanol, 1-propanol, 2-butanol, 2-methyl-1-propanol, 2-propanol, 3-methyl-1-butanol, acetic acid, acetone, anisole, butyl acetate, dimethyl sulfoxide, ethanol, ethyl acetate, ethyl ether, ethyl formate, formic acid, heptane, hexane, isobutyl acetate, isopropyl acetate, methyl acetate, methylethyl ketone, methylisobutyl ketone, pentane, propyl acetate, tert-butylmethyl ether, diisopropyl ether, methyl tert-butyl ether, methylisopropyl ketone, and methyltetrahydrofuran.

In some embodiments, two or more pharmaceutically acceptable solvents are mixed to provide the pharmaceutically acceptable solvent.

In some embodiments, the birch bark is contacted with n-heptane at a temperature of between about 60° C. and 130° C. for between 8 to 12 minutes.

In some embodiments, the (a) contacting birch bark with a pharmaceutically acceptable solvent to form an extraction solution comprising betulin and one or more triterpenes and (b) separating the birch bark from the extraction solution are run using a continuous extraction process (Shown in FIG. 2).

In one embodiment of the continuous extraction process, birch bark is mixed with n-heptane in a proportion of about 1:14 to 1:16 (w/v). The mixture is extracted continuously using n-heptane as extraction solvent at a temperature of about 115-130° C. and at a pressure of about 4.5 bar (Nitrogen). At the lower end of the sedimentation vessel the extracted cork is rinsed down by cold n-heptane, and at the upper end of the sedimentation vessel the extract (hot solution of triterpenes in n-heptane) is filtrated (10 µm filter) and transported through a second filter (1 µm filter) to the crystallisation step.

In some embodiments, the cooling of step (c) is carried out at a temperature of about −20° C. to about 35° C., about −15° C. to about 35° C., −10° C. to about 35° C., about −5° C. to about 35° C., or about 0° C. to about 35° C. In other embodiments, in step (c) the cooled extraction solution is supersaturated at least about 1-fold, about 2-fold, about 3-fold, about 4-fold, about 5-fold or about 6-fold. In preferred embodiments, in step (c) the cooled extraction solution is supersaturated about 2-fold or about 5-fold.

In some embodiments, the drying step (e) is carried out under vacuum at a temperature of at least 50° C., at least 60° C., at least 70° C., at least 80° C. or at least 85° C. In certain embodiments, the drying step (e) is carried out at a temperature of about 65° C. to about 75° C., about 70° C. to about 80° C., about 75° C. to about 85° C., or about 85° C. to about 95° C.

In some embodiments, the drying step (e) is carried out under vacuum at a pressure of less than about 90 mbar, less than about 80 mbar, less than about 70 mbar, less than about 60 mbar or less than about 50 mbar. In certain embodiments, drying step (e) reduces the amount of the pharmaceutically acceptable solvent in the dry birch bark extract to less than about 0.5% (weight/weight).

The present invention also provides the solid birch bark extracts prepared according to the processes set forth above.

Compositions Comprising Solid Birch Bark Extracts

The present disclosure provides clinically-advantageous wound-healing formulations comprising solid birch bark extracts. The compositions include oleogels, emulsions, foams, and oleogel-impregnated sterile wound dressings. The compositions are useful as topical wound healing agents.

Gels are finely dispersed systems comprising a liquid phase and a solid phase. The solid phase forms a coherent three-dimensional framework and the two phases permeate one another. Oleogels are hydrophobic gels based on a nonpolar liquid (for example, an oil, a wax, or a paraffin) to which a gel-forming agent is added to achieve the desired physical properties.

The present disclosure provides oleogels comprising a nonpolar liquid and an oleogel-forming agent. Suitable nonpolar liquids for use in oleogels of the present disclosure include, for example, plant, animal, or synthetic oils, waxes, and paraffins. In some embodiments, the nonpolar liquid is a vegetable oil selected from the group consisting of: castor oil, peanut oil, jojoba oil, sunflower oil, olive oil, avocado oil, and almond oil. In a preferred embodiment, the nonpolar liquid is sunflower oil.

In some embodiments, the nonpolar liquid comprises at least one triglyceride. In certain embodiments, the at least one triglyceride is Miglyol. In other embodiments, the nonpolar liquid comprises at least one C7 or greater hydrocarbon. In certain embodiments, the at least one C7 or greater hydrocarbon is a paraffin.

In some embodiments, the nonpolar liquid used in the oleogel has a peroxide value of lest than about 15, less than about 10, less than about 5, less than about 4, less than about, 3 or less than about 2. In certain embodiments, the nonpolar liquid has a peroxide value of no more than about 3. The term "peroxide value" as used herein means the peroxide value is determined according to Ph. Eur. 2.5.5.

The present disclosure provides methods of making oleogels. In some embodiments, after the solid birch bark extract is dried, about 1 wt % to about 20 wt % of the dried solid birch bark extract is dispersed in nonpolar liquid to form an oleogel. In certain embodiments, the nonpolar liquid is sunflower oil.

In certain embodiments, the oleogel is sterile. The oleogel may be sterilized by suitable methods known to those skilled in the art, for example using ionizing radiation such as electron beam (EB), X-ray, or gamma. In some embodiments, the oleogel is sterilized by ionizing (e.g., gamma) irradiation at doses less than about 40 kGy, less than about 35 kGy, less than about 30 kGy, less than about 25 kGy, less than about 20 kGy, or less than about 15 kGY. In certain embodiments, the oleogel is sterilized by ionizing (e.g., gamma) irradiation at doses ranging from about 5 to about 25 kGy, about 9 to about 25 kGy, about 10 to about 25 kGy, about 11 to about 25 kGy, about 12 to about 25 kGy, or from about 11 to about 20 kGy.

In some embodiments, the oleogel comprises between about 1 wt. % and about 30 wt. % solid birch bark extract dispersed in about 70 wt. % to about 99 wt. % of one or more nonpolar liquids, wherein the oleogel contains at least one oleogel forming agent in addition to the solid birch bark extract particles. In some embodiments, the oleogel comprises between about 1 wt. % and about 20 wt. % solid birch bark extract dispersed in about 80 wt. % to about 99 wt. % of one or more nonpolar liquids, wherein the oleogel contains at least one oleogel forming agent in addition to the solid birch bark extract particles.

In other embodiments, the oleogel comprises between about 1 wt. % and about 30 wt. % solid birch bark extract particle dispersed in about 70 wt. % to about 99 wt. % of one or more nonpolar liquids, wherein the dispersed solid birch bark extract particles are the only oleogel forming agent in the oleogel. In some embodiments, the oleogel comprises between about 1 wt. % and about 20 wt. % solid birch bark extract dispersed in about 80 wt. % to about 99 wt. % of one or more nonpolar liquids, wherein the oleogel contains at least one oleogel forming agent in addition to the solid birch bark extract particles.

In certain embodiments, the oleogel comprises: about 5 wt. % solid birch bark extract particle dispersed in about 95 wt. % of one or more nonpolar liquids; about 10 wt. % solid birch bark extract particle dispersed in about 90 wt. % of one or more nonpolar liquids; about 15 wt. % solid birch bark extract particle dispersed in about 85 wt. % of one or more nonpolar liquids; or about 20 wt. % solid birch bark extract particle dispersed in about 80 wt. % of one or more nonpolar liquids.

In the foregoing embodiments, the amount of solid birch bark extract particle (for example, about 1 wt. % and about 20 wt. %) includes up to about 0.5 wt % of solid birch bark extract particles that are dissolved in the nonpolar liquid.

Stressing an oleogel by centrifugation provides information on the tendency of the oleogel to separate (or segregate) the nonpolar liquid. In some embodiments of the oleogels of the present disclosure, the segregation of the nonpolar liquid from the oleogel is less than about 10%, about 9%, about 8%, about 7%, about 6%, about 5%, about 4%, about 3%, about 2%, about 1%, about 0.5%, or about 0.1% after centrifuging at 25° C. for about 30 minutes at 2750 g (e.g., 4,400 rpm).

The oleogels of the present disclosure may be characterized by their viscosity. In certain embodiments, the viscosity at 200/s of the oleogel ranges from about 0.5 to about 4.0 Pa·s and the thixotropy value of the oleogel ranges from about 200 to about 1200 Pa·s as measured according to the rotating viscometer method described in Ph. Eur. 2.2.10 using a cone-plate viscometer.

The oleogels of the present disclosure may be also characterized by their consistency values as determined using a texture analyzer. Texture analysis is primarily concerned with measurement of the mechanical properties of a product calculated from the results of a two cycle texture profile analysis test. Texture analysers perform this test by applying controlled forces to the product and recording its response in the form of force, deformation and time.

In present disclosure, consistency is the force [mN] needed to penetrate 1 cm into a sample (e.g., oleogel) as measured using a material testing apparatus (Texture analyser) with a cylindrical penetrating object (0.5 inch=1.27 cm). The speed of penetration is 0.4 mm/s.

The oleogels of the present disclosure may be distinguished from simple thickened mixtures of the solid birch bark extracts on the basis of consistency values. Specifically, the oleogels of the present disclosure may be characterized by having a consistency value of less than about 3000 mN, and at least about 250 mN as measured by a texture analyzer. In some embodiments, the consistency value of the oleogels is between about 300-2000 mN as measured by a texture analyser.

The present disclosure also provides methods for preparing oleogels. In some embodiments, the method comprises dispersing solid birch bark extract in a suitable nonpolar liquid.

In some embodiments, a sterile wound dressing comprising a pad and a therapeutically effective layer comprising the oleogel of the present disclosure is provided. In certain embodiments, the pad is an adsorbent pad. In other embodiments, the pad is any solid material suitable for covering a wound, including cotton gauze. In some embodiments, the therapeutically effective layer of oleogel is applied to one or more surfaces of the pad (e.g., the surface of the pad intended to contact the skin or wound of the patient directly). In other embodiments, the pad is immersed in the oleogel such that the oleogel is disposed on at least a portion of the outer surfaces of the pad, and optionally in at least portions of the interior of the pad.

In some embodiments, the pad can comprise a material suitable for dressing a wound that dissolve when used, releasing the oleogel. Such materials can include absorbable materials comprising collagen, alginate, etc.

The term emulsion relates to heterogeneous systems consisting of two liquids that are not miscible with each other or only miscible to a limited extent, which are typically designated as phases. In an emulsion, one of the two liquids is dispersed in the other liquid in the form of minute droplets.

In some embodiments, an emulsion comprising the solid birch bark extract of the present disclosure is provided. Other embodiments provide emulsions comprising the oleogels of the present disclosure.

In some embodiments, the emulsions of the present disclosure include an emulsifier. In certain embodiments, the emulsifier is (hydropropyl)methyl cellulose. In certain other embodiments, the emulsions are substantially free of an emulsifier.

For treating skin wounds, foams may be superior to oleogels because foams can be applied to wounds almost touchless whereas the application of an oleogel requires touch. Foams are generally based on emulsions where a propellant is mixed with the dispersed lipid phase of an emulsion.

The present disclosure provides foams comprising a solid birch bark extract-containing emulsion as described above.

In certain embodiments, the foam comprises an oleogel consisting of about 5 wt. % to about 10 wt. % solid birch bark extract and the emulsion is a water-in-oil emulsion consisting of the oleogel and about 20 wt. % to about 30 wt. % of water.

In certain other embodiments, the foam comprises an oleogel consisting of about 7 wt. % solid birch bark extract and the emulsion is a water-in-oil emulsion consisting of the oleogel and about 25 wt. % of water.

In certain embodiments, the foams of the present disclosure further comprise an emulsifier. Emulsifiers are well known in the art as substances that stabilize emulsions, and include surfactants. Emulsifiers useful in the present invention are those that are acceptable for pharmaceutical use, particularly for skin or wound contact. In some embodiments, suitable emulsifiers include emulsifying waxes, cetearyl alcohol, polysorbate 20, ceteareth 20, etc. In certain further embodiments, the emulsifier is selected from the group consisting of phosphatidyl choline, polyglyceryl-3-methyl glucose distearate, and combinations thereof.

In certain embodiments, the oleogels, emulsions, and foams of the present disclosure further comprise a disinfectant. In certain further embodiments, the disinfectant is selected from the group consisting of ethanol, propan-1-ol (n-propanol), and propan-2-ol (isopropanol). In other embodiments, the oleogels, emulsions, and foams of the present disclosure further comprise an antibiotic, particularly lipophilic antibiotics such as fluoroquinolones, macrolides, tigecycline, lincosamides, rifampin, linezolid, tetracyclines, and chloramphenicol.

In certain embodiments, the foams of the present disclosure possess certain physical properties. In some embodiments, the foam index is greater than about 2. In other embodiments, the emulsion used in the foam exhibits an interfacial surface tension of greater than about 4 nM/m using methods known in the art. The term "foam index" as used herein is the ratio of the foamed and unfoamed densities of the specified material. For example, the foam index of a particular foam is the ratio of the density of the foamed material to the density of the material prior to foaming.

The present disclosure also provides for pressurized containers filled with an emulsion of the present invention and a pharmaceutically acceptable propellant whereby the emulsion forms a foam upon decanting at least a portion of the mixture from the container.

Methods of Using Solid Birch Bark Extracts

The present disclosure also provides methods of treating a wound in a patient by topically administering an effective amount of an oleogel, an emulsion or a foam of the present disclosure to at least a portion of the wound.

In certain embodiments, the wound treated is selected from the group consisting of burns (such as mild to severe burns), surgical skin lesions, superficial injuries, chronic wounds (such as pressure ulcers, diabetic foot ulcers, chronic venous ulcers, artery insufficiency ulcers, etc.), aesthetic skin treatments (such as ablative laser skin treatments, chemical peels, dermabrasion, etc.), wounds resulting from adverse drug reactions (such as toxic epidermal necrolysis, Lyell syndrome, Stevens-Johnson syndrome, radiation-induced dermatitis, chemotherapy-induced dermatitis, etc.), rare skin diseases (such as epidermolysis bullosa, pemphigus vulgaris, pemphigoid, bullous pemphigoid, pemphigus foliaceus, pyoderma gangrinosa, etc.) and combinations thereof.

The present disclosure also provides methods of treating epidermolysis bullosa in a patient in need thereof comprising topically administering an effective amount of an oleogel, an emulsion or a foam of the present disclosure to an area of epidermolysis bullosa of the patient.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

What is claimed is:

1. A method of treating a wound associated with epidermolysis bullosa in a patient in need thereof, comprising topically administering a sterile oleogel to the wound,
    wherein the oleogel comprises about 1 wt. % to about 20 wt. % of particles of a solid birch bark extract dispersed in one or more nonpolar liquids;
    wherein the solid birch bark extract comprises at least about 70 wt. % betulin and one or more triterpenes selected from the group consisting of betulinic acid, oleanolic acid, erythrodiol, and lupeol; and
    wherein the oleogel is sterilized by ionizing irradiation at doses ranging from about 11 to about 40 kGy.

2. The method of claim 1, wherein the oleogel has a consistency ranging from about 300-3000 mN; wherein the consistency is the force (mN) needed to penetrate 1 cm into the oleogel as measured using a texture analyser with a 1.27 cm cylindrical penetrating object, and the speed of penetration is 0.4 mm/s.

3. The method of claim 1, wherein the oleogel is prepared by a process comprising dispersing the about 1 wt. % to about 20 wt. % of a dried solid birch bark extract in the one or more non-polar liquids; and wherein the nonpolar liquid has a peroxide value less than about 3.

4. The method of claim 1, wherein the oleogel is sterilized by ionizing irradiation at doses ranging from about 11 to about 20 kGy.

5. The method of claim 1, wherein the ionizing radiation is X-ray or gamma radiation.

6. The method of claim 1, wherein the dispersed solid birch bark extract particles are the only oleogel forming agent in the oleogel.

7. The method of claim 1, wherein the oleogel comprises about 10 wt. % of particles of the solid birch bark extract.

8. The method of claim 1, wherein the nonpolar liquid comprises one or more vegetable oils.

9. The method of claim 8, wherein the nonpolar liquid is sunflower oil.

10. The method of claim 1, wherein the oleogel is substantially free of solid birch bark extract particles having a size greater than about 50 μm.

11. A method of treating a wound associated with epidermolysis bullosa in a patient in need thereof, comprising:
(a) applying a sterile oleogel to the surface of a dressing and
(b) contacting the wound with the dressing such that the oleogel is in direct contact with the wound;
wherein the sterile oleogel comprises about 1 wt. % to about 20 wt. % of particles of a solid birch bark extract, dispersed in one or more nonpolar liquids;
wherein the solid birch bark extract comprises at least about 70 wt. % betulin and one or more triterpenes selected from the group consisting of betulinic acid, oleanolic acid, erythrodiol, and lupeol; and
wherein the oleogel is sterilized by ionizing irradiation at doses ranging from about 11 to about 40 kGy.

12. The method of claim 11, wherein the oleogel has a consistency ranging from about 300-3000 mN; wherein the consistency is the force (mN) needed to penetrate 1 cm into the oleogel as measured using a texture analyser with a 1.27 cm cylindrical penetrating object, and the speed of penetration is 0.4 mm/s.

13. The method of claim 11, wherein the oleogel is prepared by a process comprising dispersing the about 1 wt. % to about 20 wt. % of a dried solid birch bark extract in the one or more non-polar liquids; and wherein the nonpolar liquid has a peroxide value less than about 3.

14. The method of claim 11, wherein the oleogel is sterilized by ionizing irradiation at doses ranging from about 11 to about 20 kGy.

15. The method of claim 11, wherein the ionizing radiation is X-ray or gamma radiation.

16. The method of claim 11, wherein the dispersed solid birch bark extract particles are the only oleogel forming agent in the oleogel.

17. The method of claim 11, wherein the oleogel comprises about 10 wt. % of particles of the solid birch bark extract.

18. The method of claim 11, wherein the nonpolar liquid comprises one or more vegetable oils.

19. The method of claim 18, wherein the nonpolar liquid is sunflower oil.

20. The method of claim 11, wherein the oleogel is substantially free of solid birch bark extract particles having a size greater than about 50 μm.

21. A method of treating a wound associated with epidermolysis bullosa in a patient in need thereof, comprising:
(a) applying a sterile oleogel to the wound and
(b) covering the wound with a dressing;
wherein the sterile oleogel comprises about 1 wt. % to about 20 wt. % of particles of a solid birch bark extract, dispersed in one or more nonpolar liquids;
wherein the solid birch bark extract comprises at least about 70 wt. % betulin and one or more triterpenes selected from the group consisting of betulinic acid, oleanolic acid, erythrodiol, and lupeol; and
wherein the oleogel is sterilized by ionizing irradiation at doses ranging from about 11 to about 40 kGy.

22. The method of claim 21, wherein the oleogel has a consistency ranging from about 300-3000 mN; wherein the consistency is the force (mN) needed to penetrate 1 cm into the oleogel as measured using a texture analyser with a 1.27 cm cylindrical penetrating object, and the speed of penetration is 0.4 mm/s.

23. The method of claim 21, wherein the oleogel is prepared by a process comprising dispersing the about 1 wt. % to about 20 wt. % of a dried solid birch bark extract in the one or more non-polar liquids; and wherein the nonpolar liquid has a peroxide value less than about 3.

24. The method of claim 21, wherein the oleogel is sterilized by ionizing irradiation at doses ranging from about 11 to about 20 kGy.

25. The method of claim 21, wherein the ionizing radiation is X-ray or gamma radiation.

26. The method of claim 21, wherein the dispersed solid birch bark extract particles are the only oleogel forming agent in the oleogel.

27. The method of claim 21, wherein the oleogel comprises about 10 wt. % of particles of the solid birch bark extract.

28. The method of claim 21, wherein the nonpolar liquid comprises one or more vegetable oils.

29. The method of claim 28, wherein the nonpolar liquid is sunflower oil.

30. The method of claim 21, wherein the oleogel is substantially free of solid birch bark extract particles having a size greater than about 50 μm.

* * * * *